United States Patent [19]

Atkinson et al.

[11] Patent Number: 5,573,923

[45] Date of Patent: *Nov. 12, 1996

[54] METHOD FOR REMOVING N-TERMINAL DIPEPTIDES FROM PRECURSOR POLYPEPTIDES WITH IMMOBILIZED DIPEPTIDYLAMINOPEPTIDASE FROM DICTYOSTELIUM DISCOIDEUM

[75] Inventors: Paul R. Atkinson, Indianapolis; Lisa K. Foster, Greenwood, both of Ind.

[73] Assignee: Eli Lilly and Company, Indianapolis, Ind.

[*] Notice: The term of this patent shall not extend beyond the expiration date of Pat. No. 5,565,330.

[21] Appl. No.: 172,501

[22] Filed: Dec. 22, 1993

[51] Int. Cl.⁶ .............................. C12P 21/06; C12N 9/48; C12N 9/58

[52] U.S. Cl. .................. 435/68.1; 435/212; 435/223

[58] Field of Search ................................ 435/68.1, 223, 435/174, 178, 212

[56] References Cited

U.S. PATENT DOCUMENTS 5,126,249  6/1992  Becker et al. ..................... 435/68.1

FOREIGN PATENT DOCUMENTS

0217814B1  5/1990  European Pat. Off. .

OTHER PUBLICATIONS

Chan, et. al., 1985, *Biochem. Biophys. Res. Comm.*, 127(3) : 962–968.
Chan, et. al., 1987, *Experimental Mycology*, 11:27–35.
Huang, et. al., 1992, *Experimental Mycology*, 16:102–109.
Hutchinson et al, (1987) *Biochim. Biophys. Acta.*, 916, 1–4.
Erickson et al, (1983) *Biochim. Biophys. Acta.*, 743, 37–42.

*Primary Examiner*—Michael G. Wityshyn
*Assistant Examiner*—Jon P. Weber
*Attorney, Agent, or Firm*—Ronald S. Maciak; David E. Boone

[57] ABSTRACT

A method for removing dipeptides from the amino terminus of precursor polypeptides to produce a polypeptide product is presented which comprises contacting the precursor polypeptide for sufficient time to remove the dipeptide with an immobilized dipeptidylaminopeptidase (dDAP) from the slime mold, *Dictyostelium discoideum*, which has a mass of about 225 kilodaltons and a pH optimum of about 3.5. The precursor polypeptides may be made recombinantly and may be analogs of naturally occurring polypeptides.

20 Claims, No Drawings

METHOD FOR REMOVING N-TERMINAL DIPEPTIDES FROM PRECURSOR POLYPEPTIDES WITH IMMOBILIZED DIPEPTIDYLAMINOPEPTIDASE FROM DICTYOSTELIUM DISCOIDEUM

FIELD OF THE INVENTION

This invention was made in the field of biotechnology and concerns a method of using immobilized dipeptidylaminopeptidase isolated from the slime mold, *Dictyostelium discoideum*. The invention is useful for processing proteins having an even numbered amino acid N-terminal extension.

BACKGROUND OF THE INVENTION

*Dictyostelium discoideum* is a primitive eukaryotic microorganism commonly called a slime mold, or more specifically, a cellular slime mold. The name is derived from the two extreme states of the microorganism from a macroscopic perspective. When actively growing, *D. discoideum* grows as single cell amoeba. At this stage the organism has no cell wall, hence it appears as a thin film (or slime). Upon starvation on a solid medium, the independent cells aggregate to form a colony. The colony exhibits traits of a multicellular organism in that it migrates in the form called a slug and then differentiates, with the posterior cells of the slug forming a foot, the anterior cells forming a stalk and the middle cells forming a fruiting body. The organism is found naturally on the surface of soil and dung. The wild type amoeba obtains nutrients exclusively by ingestion (phagocytosis) of whole bacteria; for this reason, the organism is sometimes referred to as carnivorous. Axenic mutants of *D. discoideum* have been isolated which are capable of growth without coculture of "food" bacteria and which therefore can be grown on soluble media. The present invention relates to the immobilization and use of a novel dipeptidylaminopeptidase (DAP) isolated from *D. discoideum*.

Dipeptidylaminopeptidases are enzymes which hydrolyze the penultimate amino terminal peptide bond releasing dipeptides from the unblocked amino-termini of peptides and proteins. There are currently four classes of dipeptidylaminopeptidases (designated DAP-I, DAP-II, DAP-III and DAP-IV) that differ based on their physical characteristics and the rates at which they react with their substrates. DAP I is a relatively non-specific DAP that catalyzes the release of many dipeptide combinations from the unblocked amino termini of peptides and proteins. DAP I shows little or no activity if the emergent dipeptide is X-Pro, Arg-X, or Lys-X (where X is any amino acid). DAP II shows a preference for amino terminal dipeptide sequences that begin with Arg-X or Lys-X, and to a lesser extent, X-Pro. DAP-II exhibits significantly lower reaction rates versus most other dipeptide combinations. DAP III appears to have a propensity toward amino terminal dipeptide sequences of the form Arg-Arg and Lys-Lys. DAP IV shows its highest rate of hydrolytic activity toward dipeptide sequences of the form X-Pro. The DAP enzymes, particularly DAP-I and DAP-IV, have been shown to be useful in processing proteins.

The present invention concerns a novel DAP isolated from *Dictyostelium discoideum* (dDAP), which is the subject of U.S. patent application Ser. No. 07/955,539. More significantly, the present invention represents an improved method for processing proteins having an even numbered amino acid N-terminal extension. The older method is a single-use batch reaction in which dDAP is added to substrate and allowed to react for a specified time. Subsequent purification steps were needed to ensure removal of dDAP from the product stream. The improvement over single-use batch conversion reactions is a result of immobilizing dDAP to relatively inexpensive and commercially available chromatography resins to selectively immobilize dDAP in an active form.

It was most surprisingly found that dDAP strongly binds to anion exchange resins under acidic conditions where most proteins either do not bind or only bind weakly. Under acidic conditions where anion exchange resins typically are not used, dDAP is both stable and highly active against certain substrates of interest. The acidic pH effectively prevents the subsequent binding of substrate and product to this resin at levels high enough to impact yield or at levels high enough to displace the non-covalently attached enzyme. The effective concentration of dDAP on the resin can be made quite high enabling relatively rapid reaction kinetics. The present invention decreases the time that reactants and products are exposed to harsh conditions of pH and temperature that adversely impact reactant and product stability, yield, purity, and structure. Moreover, the present process provides a convenient means for reusing dDAP in later conversion reactions. Thus, the benefit of the improved process of the present invention is to reduce the overall amount of enzyme required to convert a given amount of precursor protein and to reduce the time that reactants and products are exposed to harsher batch process conditions.

SUMMARY OF THE INVENTION

The present invention is a method for removing aminoterminal dipeptides from a precursor polypeptide or protein to produce a processed polypeptide or protein. The method begins by immobilizing *Dictyostelium discoideum* dipeptidylaminopeptidase on a suitable solid support. The immobilized dDAP is then contacted with the precursor polypeptide under conditions sufficient to allow the action of dDAP to sequentially remove the amino-terminal dipeptides from the precursor polypeptide. The method concludes by recovering the processed polypeptide. In another embodiment, the method is useful for removing a single amino-terminal dipeptide from a precursor polypeptide to produce a processed polypeptide.

DETAILED DESCRIPTION OF THE INVENTION

For purposes of the present invention, as disclosed and claimed herein, the following terms and abbreviations are defined below.

dDAP—a dipeptidylaminopeptidase, isolated from *Dictyostelium discoideum*, which demonstrates a pH optimum of about pH 3.5 using GFpNA as the substrate and has a native molecular weight of about 225,000 daltons, as measured by analytical ultracentrifugation, and a subunit molecular weight of about 66,000 daltons, as measured by SDS polyacrylamide gel electrophoresis (SDS-PAGE).

Precursor polypeptide—a polypeptide or protein which comprises an even number of amino acids extended from the amino terminus of the desired polypeptide of interest.

Processed polypeptide—a polypeptide or protein wherein the N-terminal dipeptide or dipeptides have been removed to yield the desired polypeptide of interest.

Support surface—any solid or semi-solid surface or matrix that can be used as is or easily derivatized or activated to bond a protein, exhibits minimal non-specific adsorption, is physically mechanically and chemically stable, is highly porous to provide ligand accessibility, and can be regenerated without deteriorating the surface.

dDAP bed—any amount of dDAP immobilized to a single or multiple support surface that forms an aggregate volume or unit of immobilized dDAP.

MR-KPB-hPI—Defined as Met-Arg-Human Proinsulin having Lys at position 28 and Pro at position 29 of the corresponding insulin B-chain. This human insulin analog precursor protein may also be expressed in the following nomenclature style; Met-Arg-Human Proinsulin Analog (B28 Lys, B29 Pro).

KPB-hPI—Defined as Human Proinsulin having Lys at position 28 and Pro at position 29 of the corresponding insulin B-chain. This human insulin analog processed protein may also be expressed in the following nomenclature style; Human Proinsulin Analog (B28 Lys, B29 Pro).

GFpNA—Gly-Phe p-nitroanilide.

RRBNA—Arg-Arg-β-naphthylamide.

Z-RRBNA - Benzyioxycarbonyl-RRBNA

All amino acid abbreviations used in this disclosure are those accepted by the United States Patent and Trademark Office as set forth in 37 C.F.R. §1.822(b)(2) (1992).

The present invention relies on the physical, chemical, and enzymatic properties of dDAP which is the subject of U.S. patent application Ser. No. 07/955,539, herein incorporated by reference. Some of the more salient characteristics of dDAP include a propensity to cleave unblocked amino terminal dipeptides, a pH optimum of about pH 3.5 using GFpNA as the substrate, no significant enzymatic activity above pH 6, a native molecular weight of about 225,000 daltons, and a subunit molecular weight of about 66,000 daltons. The dDAP enzyme has the ability to remove dipeptides from the synthetic substrates, GFpNA and RRBNA, as well as from numerous other natural, synthetic and recombinantly-produced polypeptides. Moreover, dDAP is able to cleave amino terminal dipeptides in which the N-terminal amino acid is an oxidized methionyl residue (i.e. Met(O)-Arg-Human Proinsulin). The dDAP enzyme requires no added reducing agents and is fully active in the presence of cysteine modifiers such as iodoacetate or tetrathionate.

The present invention is particularly useful for efficiently converting precursor polypeptides or proteins into processed polypeptides or proteins. For instance, if human growth hormone is the desired polypeptide, one merely expresses a precursor of human growth hormone (in one case, a Met-Asp-human growth hormone), then subjects this precursor to dDAP activity to release the dipeptide Met-Asp and the desired processed polypeptide, human growth hormone. The processed peptide is not required to be the "natural" wild-type polypeptide, as often it is desirable to produce analogs or intermediates. Other precursor polypeptides which may be processed using the present invention include Met-Arg-human growth hormone, Met-Arg-Human Proinsulin, Met-Tyr-Human Proinsulin, Met-Arg-Human Proinsulin Analog (B28 Lys, B29 Pro), Met-Tyr-Human Proinsulin Analog (B28 Lys, B29 Pro), Met-Arg-Human Proinsulin Analog (B10 Asp, des B28-30), Met-Tyr-Human Proinsulin Analog (B10 Asp, des B28-30), and Met-Tyr-Human Proinsulin Analog (des 64). Insulin Analog (B28 Lys, B29 Pro) is disclosed in European Patent Application Serial No. 90301224.3 while Insulin Analog (B10 Asp, des B28-30) is disclosed in European Patent Application Serial No. 92305678.2.

Processing of Met-Arg-Human Proinsulin and Met-Arg-Human Proinsulin Analogs with bovine DAP-I is disclosed in Becker et. al., U.S., Pat. No. 5,126,249, issued Jun. 30, 1992, the entire teaching of which is herein incorporated by reference. In addition, dDAP may be used to sequentially remove more than one set of dipeptides from the N-terminus of precursor polypeptides.

Using dDAP to remove dipeptides from precursor proteins is advantageous because dDAP has a pH optimum of about 3.5 which allows the reaction to be run at acidic pH ranges where many precursor polypeptides will be soluble. Furthermore, conversions of some precursor polypeptides at neutral pH or higher may lead to higher levels of interchain disulfide dimers or polymers of the substrate, with a concomitant loss in product yield. This phenomenon, known as disulfide scrambling, is particularly troubling when one uses bovine DAP-I, as DAP-I requires the addition of reducing agents, such as β-mercaptoethanol or cysteine, to the reaction mixture. Also, oxidation of methionine residues occurs at a lower rate in acidic pH ranges.

Fermentation of *D. discoideum* axenic strain AX-3 (ATCC 28368) followed by centrifugation, anion exchange chromatography, hydrophobic interaction chromatography and size exclusion chromatography yields a highly purified solution of dDAP enzyme that can be stored at −20° C. in the presence of 55% v/v glycerol, 0.025M acetic acid, 0.25M sodium chloride, pH 3.5 or can be used immediately in the method of the present invention.

To make and use the present invention, it is first necessary to immobilize purified dDAP onto a suitable solid support surface or matrix. The ordinarily skilled artisan will readily understand and appreciate the many commercially-available solid support surfaces and matrices. By way of illustration not meant to limit the scope of the invention, solid support surfaces may include inorganic materials such as porous silica, controlled pore glass, and hydroxyapatite. Synthetic organic polymers such as polyacrylamide, polymethacrylate, and polystyrene are also illustrative support surfaces. In addition, polysaccharides such as cellulose, dextran, Sephadex®, beaded dextran, Sepharose®, beaded agarose, and agarose are further illustrative examples of support surfaces consistent with the invention. Other support surfaces such as membranes and fibers are also consistent with the claimed process. An example of a commercially available membrane is the Acti-Mod®, polyvinylchloride membrane impregnated with silica, quaternary amine module (FMC BioProducts).

Preferred support surfaces are those which do not adversely affect dDAP once bound to the surface. Commercially-available polysaccharide matrices formed into various sized beads are more preferred because they are porous, easy to handle, and are well known and understood in the biochemical purification art. More highly preferred support surfaces are commercially-available anion exchange resins. The most preferred support surface is Q Sepharose® resin, trimethylaminomethyl substituted beaded agarose, (Pharmacia). See *Affinity Chromatography Principles & Methods*, Pharmacia Fine Chemicals, (1983); *Biotechnology/Products Catalog* 1993, Pharmacia Biotech Inc, 800 Centennial Ave., Piscataway, N.J. 08854.

A wide assortment of schemes for immobilizing or coupling proteins to support surfaces has developed over the past few decades. Both covalent and non-covalent immobilization of dDAP to the support surface is consistent with the invention as are bridges that serve to link the support surface to the dDAP enzyme.

Enzyme immobilization is most usually accomplished using solid supports, generally chromatography resins, that have been modified or activated to include functional groups that permit the covalent coupling of resin to enzyme. Typically aliphatic linker arms are employed. An example of a commercially available covalent immobilization resin is Activated CH Sepharose® 4B, 6-amino-hexanoic acid substituted beaded agarose, (Pharmacia). It is one of many types of chemistries that Pharmacia has attached to the Sepharose® 4B base matrix. In general, activated resins cost significantly more than anion exchange resins of the same base matrix, are not available in as wide of a variety of base matrix types as ion exchange chromatographic media and may therefore be more limited in their ability to handle low clarity column charges or high mobile phase flow rates.

CNBr and carbodiimide coupling of proteins to polysaccharide based beads such as Sepharose® (Pharmacia) are also illustrative of direct coupling schemes consistent with the invention. Direct couplings generally do not orient the bound proteins in any particular fashion; however, some types of direct couplings are able to reproducibly orient the bound protein onto the support surface.

The dDAP enzyme may also be noncovalently attached to a solid support surface, through, for example, ionic or hydrophobic mechanisms. A large variety of ion exchange and hydrophobic interaction chromatography resins are available from a large number of commercial sources, at lower cost than the activated, covalent immobilization resins.

A potential drawback to noncovalent immobilization is that the enzyme binding is usually reversible. Moderate levels of salts, solvents, pH change or even other proteins can lead to partial or complete desorption of the enzyme from the resin. In most instances, it would be difficult to identify conditions in which enzyme binding to noncovalent resins is tight, in which the enzyme maintains a high degree of functional activity and stability, and in which the enzyme reactants do not themselves bind to the resin.

Most unexpectedly, a key element in the presently disclosed invention was the highly opposed affinities of dDAP and MR-KPB-hPI for an anion exchange resin at the acidic pH at which dDAP is maximally active. Based on chromatographic behavior and isoelectric focusing, dDAP is believed to have an abundance of negative charges at acidic pH. Consequently, it is believed that dDAP binds strongly to the cationic functional groups of anion exchange resins, while MR-KPB-hPI or proinsulin do not bind even when they are present in large stoichiometric excess.

However, the reversibility of noncovalent enzyme binding also represents an advantage over covalent immobilization. Generally, noncovalent resin binding can be easily and repeatedly reversed. If a column resin requires regeneration because of loss of performance or increases in back pressure, the enzyme may be mildly desorbed from the resin prior to exposure of the resin to the harsh conditions of regeneration—conditions which would most likely destroy the enzyme if it remained attached to the resin. Once the resin is regenerated, it can be used to capture a new or repurified batch of enzyme.

Other immobilizing schemes may orient dDAP such that its catalytic site remains exposed. One such scheme utilizes the natural carbohydrate found on the enzyme. By first oxidizing the carbohydrate moieties to the corresponding aldehydes, then reacting the aldehyde with a primary amino group on the support surface, it is possible to link dDAP in an advantageous orientation.

Many types of bridges that connect dDAP to the support surface are possible and include small organic linkers which covalently bind dDAP to the support surface. These so called spacer arms are acceptable and preferably do not interact with proteins once the bridge has been formed.

Larger multivalent molecules bound to the support surface which are capable of binding several dDAP molecules describe another type of bridge. Specific immunoadsorbants bound to the support surface that non-covalently bind dDAP represent yet another type of bridge. Epitope specific, anti-dDAP, monoclonal antibodies are one example of a specific immunoadsorbant that is capable of orienting dDAP onto the support surface. By preparing high affinity monoclonal antibodies to a dDAP epitope distant from the catalytic site, then chemically bonding the antibody to the support surface and allowing dDAP to bind to the antibodies, it is possible to orient dDAP in a favorable configuration on the support surface.

The above discussion is in no way meant to limit the scope of the invention. The ordinarily skilled artisan will know numerous other schemes for linking proteins to support surfaces. Moreover, the choice of support surface and the method of immobilizing dDAP is largely a matter of convenience and depends on the practitioner's familiarity with, and preference for, various supports surfaces, as well as his preference for various immobilizing schemes, and knowledge of the substrate. Finally, the quantity of available dDAP and the overall purpose and setting in which precursor proteins are converted to processed proteins will influence the choice of support surface and immobilization method.

Once the dDAP has been immobilized onto a support surface, conversion of precursor polypeptides into processed polypeptides can be accomplished under a variety of suitable conditions. The preferred way is to pack a chromatography column with immobilized dDAP so that the substrate of interest (precursor protein) can be passed over the immobilized enzyme surface, allowing the reaction to proceed. Because the enzyme remains attached to the support surface, it does not become physically part of the reactant mixture and is therefore available for subsequent reuse.

It is also consistent with the present invention to repeat the contacting step one or more times to ensure complete processing of precursor protein into processed protein. Thus, the reactant/product stream may be recycled over the same dDAP bed one or more times or may be sequentially passed over seperate dDAP beds. The preferred method is to pass the precursor protein-containing stream over two or more separate dDAP beds, and it is most preferred to pass the precursor protein-containing stream over three dDAP beds prepared using Q Sepharose® resin as the support surface.

The skilled artisan will understand that the performance of an immobilized dDAP column should be monitored by following the conversion of the substrate of interest to product. Small decreases in the efficiency of the column may be improved by decreasing the column flow rate and thereby increasing the time allowed for the enzymatic reaction to occur. Ideally, the flow rate is as rapid as possible, so long as conversion of substrate to product achieves the desired yield and so long as column back pressure does not exceed operational levels. The performance of the column is also affected by column temperature and mobile phase pH. Therefore, it is advisable to monitor these parameters.

The enzymatic reaction that converts precursor polypeptides into processed polypeptides is generally conducted in an aqueous medium suitably buffered to obtain and maintain a pH from about 2.5 to about 5.5. Preferably the pH of the medium ranges from about 3.0 to about 4.5, and, most preferably, from about 3.0 to about 3.5. The pH optimum may vary slightly according to the substrate.

Using unbound dDAP, the rate of processing of GFpNA and Gly-Arg-pNA occurs most rapidly at about pH 3.5, while the rate of processing of Met-Asp-Human Growth Hormone (Met-Asp-hGH) occurs readily at about pH 3.0 to about pH 3.5. The rate of processing of RRBNA occurs most rapidly at about pH 4.5. The skilled artisan will recognize that the pH optimum of any specific reaction will be determined by such factors as stability and solubility of the given precursor polypeptide and enzyme. In some cases, a solubilizing agent such as urea, sodium dodecylsulfate, guanidine, and the like, may be employed.

Any of a wide range of buffering agents can be employed, the primary requirement being their ability to maintain a pH within the desired range and their inability to desorb the enzyme from the support surface. Examples of typical buffering agents are sodium phosphate, sodium acetate, sodium citrate, glycine, and the like. Preferred buffering agents are sodium acetate, sodium phosphate and glycine.

The precursor polypeptides for use in the present invention are generally prepared via recombinant DNA technology. In their preparation, a nucleotide sequence coding for the desired precursor polypeptide is prepared using routine techniques for such synthesis. These methods generally involve preparation of oligonucleotides coding both for fragments of the desired coding sequence and for their complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a recombinant vector at a location which permits the product for which it codes to be expressed. A suitable vector contains at least a portion of an expression control sequence.

The following Examples are provided as a means of illustrating the present invention. They are not to be construed as imposing any limitations thereon.

EXAMPLE 1

Fermentation of *Dictyostelium discoideum*

Lyophilized cultures of Dictyostelium discoideum axenic strain AX-3 were obtained from the American Type Culture Collection in Rockville, Md. under the accession number ATCC 28368 and were plated at several densities on agar plates (1.2% Difco Bacto® Agar) containing a buffered yeast extractpeptone medium composed of (g/l): Difco Yeast Extract (7.15), Difco Bacto Peptone (14.3), $Na_2HPO_4$ (0.51) and $KH_2PO_4$ (0.49), to which Glucose (10 g/l final) was added aseptically after separate sterilization and which was adjusted to a final pH of 6.5 (±0.1) with NaOH or $H_2SO_4$. This same media (without the agar) was used for liquid culture growth in volumes less than about one liter. The agar plates were incubated 3 to 5 days at 21° C. to 24° C. Spore sacks were harvested from the plate with care to prevent picking up the "food bacterium" lyophilized with the AX-3 culture, then inoculated in 3 ml of buffered yeast extract-peptone broth and incubated with gentle shaking at 21°–24° C. Thereafter, *D. discoideum* cells were amplified by serial transfer to progressively larger volumes of buffered yeast extract-peptone broth. Each serial transfer step was by a dilution between about 10- and 25-fold and occurred when cell densities exceeded about $2\times10^6$/ml. Broths were always incubated at 21°–24° C. with mild agitation.

Stirred fermentations were generally done in a similar medium with soy peptone (such as Phytone Peptone or Marcor Soy Peptone) at a concentration of 2 to 20 g/l substituted for the Bacto Peptone in the initial yeast extract-peptone medium. Glucose concentration was increased to 15 g/l total. Harvests were usually from fermentors with a working volume from 10 to 5000 liters fitted with from 1 to 3 Rushton® turbine impellors rotating at 40–150 RPM. Temperature was controlled at 22°±1° C., air flow controlled between 0.1 and 0.5 volumes air per volume of liquid broth and backpressure was maintained at 3–5 p.s.i. Fermentations were done with pH controlled between 6.3–6.5 with sulfuric acid and with dissolved oxygen controlled at 40–80% by varying agitation and/or air flow. Care was taken to minimize shear in handling and fermentation of the cells in that they are wall-less ameoba during growth.

In general, stirred cultures of *D. discoideum* A×3 grew with doubling times between 12 and 36 hours. Dissolved oxygen decreased progressively (when not controlled) and then began to rise some time after cell density stopped increasing. Terminal cell densities ranged between $3\times10^6$/ml and $1\times10^8$/ml.

Samples were taken occasionally and analyzed for cell density and dDAP activity (see Example 3, below). A Petroll-Hauser counting chamber was used to estimate cell densities above approximately $5\times10^5$ cells/ml. In general, GFpNA hydrolyzing activity increased throughout the fermentation. The maximum dDAP activity was seen 1 to 4 days after maximum cell density was reached. Whole broths were stored at 4° C. or frozen at −20° C. and later thawed and analyzed for activity. Fermentations were harvested by chilling to less than 10° C. and removing cells with a continuous-flow centrifuge.

EXAMPLE 2 dDAP Isolation

A) Cell Removal and Concentration:

Initial purification of dDAP from *Dictyostelium discoideum* fermentation broth involves cell removal and concentration steps. Cell removal was performed by continuous-flow centrifugation. The cell free media was concentrated 20–30 fold by tangential flow ultrafiltration using an Amicon regenerated cellulose 100,000 molecular weight cut-off membrane. The retentate was drained from the ultrafiltration unit and the unit was washed with 50 mM Tris® buffer, pH 7, to recover additional dDAP. The retentate and wash were combined to form a final concentrate, which was stored frozen at −20° C. for up to several months before further processing occurred.

B) Clarification:

The frozen final concentrate was thawed for about 12–24 hr at room temperature. Once thawed, the final concentrate was clarified prior to the first column chromatography step. Clarification was achieved by a combination of centrifugation followed by 1 micron membrane filtration. The clarified final concentrate was adjusted to pH 7.0 and held at 4° to 10° C.

C) Anion Exchange Chromatography:

The first chromatography step of the dDAP purification process was anion exchange chromatography using Pharmacia Q Sepharose® Fast Flow resin. The column was equilibrated with 50 mM Tris® buffer, pH 7. Clarified cell free concentrate was applied at 50 cm/hr linear flow rate. About 600–1500 units of dDAP activity were applied per liter of Q Sepharose® Fast Flow resin. The conductivity of the cell free concentrate was less than 10 mMHOS per cm. After completing the sample charge, the Q Sepharose® Fast Flow resin was washed with two column volumes of equilibration buffer. The dDAP activity was eluted from the resin using a linear gradient of 0 to 1M NaCl, 50 mM Tris®, pH 7, applied over 10 column volumes at a flow rate of 50 cm/hr. Fraction size was 0.1–0.2 column volumes. The effluent was monitored by conductivity and absorbance at 280 nm and fractions were assayed for dDAP activity by their ability to cleave the colorimetric substrate GFpNA at pH 3.5. A mainstream pool was prepared by combining fractions containing greater than 80% of the total eluted dDAP activity. The dDAP activity eluted as a single peak. The mainstream pool was acidified to a pH of 3.5 using 10% v/v HCl. The Q Sepharose® Fast Flow acidified mainstream pool was held at 4° C.

D) Hydrophobic Interaction Chromatography:

The Q Sepharose® Fast Flow acidified mainstream pool was next purified by hydrophobic interaction chromatography (HIC) on Pharmacia Phenyl Sepharose®, phenyl substituted beaded agarose, Fast Flow resin. About 500–2000 units of activity were applied per liter of resin. The Q Sepharose® Fast Flow mainstream was prepared for charge onto the HIC column by the addition of 140 grams per liter ammonium sulfate. The charge was adjusted to pH 3.5 and the final conductivity was about 90 mMHOS per cm. The HIC column was equilibrated in 50 mM citrate, pH 3.5, containing at least 140 grams per liter ammonium sulfate. The charge was applied at a linear flow rate of 40 cm/hr and the resin was washed with at least three column volumes of equilibration buffer. The dDAP activity was eluted from the resin using a linear gradient of 140 g per liter to 0 g per liter ammonium sulfate, in 50 mM citrate, pH 3.5, applied over 10 column volumes at 40 cm/hr. Fraction size was 0.1–0.2 column volumes. The effluent was monitored by conductivity and absorbance at 280 nm and fractions were assayed for dDAP activity by their ability to cleave GFpNA at pH 3.5. A mainstream pool was prepared by combining fractions containing greater than 80% of the total eluted dDAP activity. The mainstream pool was adjusted to a pH of 3.5 using 10% v/v HCl or 10% w/w NaOH. The HIC mainstream was held at 4° C.

E) Size Exclusion Chromatography:

The HIC mainstream was further processed by size exclusion chromatography (SEC) on Sephacryl® S-200 HR, acrylamide cross-linked beaded dextran. The HIC mainstream was prepared for the SEC column by concentrating the HIC mainstream in an ultrafiltration unit using an Amicon regenerated cellulose 10,000 molecular weight cut-off membrane. The HIC mainstream was concentrated and the retentate drained from the unit. The ultrafiltration unit was washed with 50 mM citrate buffer, pH 3.5. The retentate and the wash were combined to form a final concentrate and adjusted to pH 3.5 with 10% v/v HCl or 10% w/v NaOH. The final concentrate volumn was less than 2.5% of the SEC column. The conductivity of the final concentrate was about 30 mMHO per cm. The SEC column was equilibrated with 50 mM acetic acid, 0.5M sodium chloride, pH 3.5, which had a conductivity of about 20–30 mMHO per cm. The final concentrate was applied to the SEC column at 8 cm/hr linear flow and the dDAP activity was eluted by the application of one column volume of equilibration buffer. Fraction size was 0.01 column volumes. The effluent was monitored by conductivity and absorbance at 280 nm and fractions were assayed for dDAP activity by their ability to cleave GFpNA at pH 3.5. A mainstream pool was prepared by combining fractions containing greater than 80% of the total eluted dDAP activity. The dDAP activity eluted as a single peak. The SEC mainstream pool may be held at 4° C. for several months.

Purification of dDAP using a combination of anion exchange, hydrophobic interaction, and size-exclusion chromatography resulted in material that migrated as a major band on SDS-PAGE. The band migrated to a position on the gel equivalent to the molecular weight standard bovine serum albumin (66 kilodaltons). The protein was stained using ISS Pro-blue stain. The migration pattern was unaffected by the presence or absence of 0.1M dithiothreitol (plus 100° C. for 5 minutes) during sample preparation. The subunit molecular weight of DAP-I (bovine source) is estimated by SDS-PAGE to be about 22,000 daltons.

EXAMPLE 3 dDAP Activity Assay and Characterization

A) Cleavage of GF-pNA

After purification or storage, dDAP enzymatic activity was usually monitored by following the cleavage of the chromogenic substrate GFpNA. Typically the assay was performed by diluting the enzyme at least 11 fold into 1.0 ml of 4 mM GFpNA in 0.05M acetic acid adjusted to pH 3.5. The rate of cleavage of Gly-Phe dipeptide was monitored at 37° C. by measuring the increase in absorbance at 405 nm. One unit of activity leads to a 0.90 OD change per minute under these conditions. Unit/ml estimates can be made assuming an extinction coefficient for free p-nitroanilide (pNA) of 9.9 mM-1 cm-1 at 405 nm.

The inhibition profile of dDAP toward the substrate GFpNA was compared to that of bovine spleen DAP-I using iodoacetamide and potassium tetrathionate, sulfhydryl modifying agents known to inhibit the activity of bovine spleen DAP-I. Samples of dDAP or bovine spleen DAP-I were incubated for 15 minutes at room temperature in final concentrations of 0, 0.5, 5.0 or 50 mM of either inhibitor at pH 7 in 100 mM Tris buffer. The incubated solutions were then diluted 21-fold with 4 mM GFpNA, pH 3.5. The rate of cleavage was monitored by measuring the increase in absorbance at 405 nm at 37° C. Bovine DAP-I's rate of cleavage of GFpNA was decreased more than 90% by the exposure to 5 mM iodoacetamide and was 95% inhibited by 5 mM potassium tetrathionate. There was no evidence of significant inhibition of dDAP by any of the levels of iodoacetamide or potassium tetrathionate tested.

The pH optima for the GFpNA cleaving ability of dDAP was determined by adjusting a buffer consisting of 0.5M Tris®, phosphate and citrate with 10% HCl or 10% NaOH to various pHs within the range of 3 to 8. dDAP enzyme was diluted 20-fold in a buffer containing 100 mM cysteamine and 10 mM NaCl. Bovine DAP-I was diluted 200-fold in the same buffer. A GFpNA substrate solution (4 mM) was prepared in 2% dimethylformamide. In a microtiter plate, 0.025 ml of the Tris/phosphate/citrate buffer of various pH's was combined with 0.1 ml of diluted enzyme and with 0.1 ml of substrate solution. The rate of increase of absorbance at 410 nm was determined on a plate-reader over a 30 minute period. Results indicated that the pH optima of dDAP for the cleavage of GFpNA is between 3.5 and 4.0.

B) Cleavage of Gly-Arg-pNA (GRpNA)

Four mM GRpNA was prepared in 50 mM acetic acid, 50 mM glycine buffer, pH 5. HCl or NaOH was used to achieve a variety of pHs, from 5.1 to 2.3. To 180 ul of the above pH buffered substrate was added 5 ul dDAP (49 milliunits/ml final). The rate of increase of absorbance at 410 nm was monitored (using a plate-reader) and the rate of increase was compared with the pH of the reaction solution. As with GFpNA the GRpNA substrate had a pH optimum around 3.5. The enzyme had little activity below pH 2.5 or above pH 5 using this substrate.

C) Cleavage of RRBNA

About 0.25 mM RRBNA or 0.25 mM Z-RRBNA was prepared in either 100 mM acetic acid, pH 3.5, or 100 mM citrate buffer, pH 5.0. To 2 ml of substrate was added dDAP or bovine DAP-I (about 15 milliunit/ml solution). Rates of cleavage (monitoring fluorescence increase at 410 nm with excitation at 340 nm) were monitored. Bovine DAP-I was unable to cleave either substrate. Surprisingly, dDAP was able to effectively cleave the RRBNA substrate. dDAP was unable to cleave the blocked amino group Z-RRBNA substrate, supporting the observation that dDAP is a DAP enzyme. The pH optimum for cleavage of RRBNA was probed by monitoring the rate of RRBNA cleavage using a buffer system consisting of 50 mM acetic acid and 50 mM citrate. Various pHs were achieved using HCl or NaOH and 1.5 ml volumes were made 2.0 with 0.5 ml of a 1 mM stock solution of RRBNA (final concentration of about 0.25 mM). dDAP was added (to about 15 mU/ml) and the rates of cleavage were determined. The pH optimum for cleavage of RRBNA was observed to be about 4.5, with significant activity seen over the entire range probed (pH 3.5 to pH 5.7). This surprising result suggests that dDAP shares some properties with DAP III.

The skilled artisan will recognize that the optimum pH for cleavage of a substrate not only depends upon the enzyme but the substrate itself, that is, the constitution of the removed dipeptide as well as the indicator group itself. For example, using dDAP, GRpNA has a pH optimum of about 3.5 while the pH optimum for cleavage of Gly-Arg-7-amido-4-methylcoumarin is about pH 5, suggesting that the reporting group can effect the cleavage properties.

EXAMPLE 4 dDAP Column Preparation

A 1.0 ml (0.5×5.0 cm) column of Q Sepharose® Fast Flow resin (Pharmacia) was packed and equilibrated with 10 column volumes of dilute acetic acid (0.05M acetic acid, pH 3.5). A 1 unit per ml solution of dDAP (prepared in accordance with Examples 1 and 2, 5.5 U per ml) was prepared by diluting a 0.27 ml volume of dDAP into 1.22 ml of dilute acetic acid. The dDAP solution was applied at a flow rate of 30 cm/hr (0.1 ml per minute) and the column was washed with at least 10 ml of additional dilute acetic acid. The column flow-through was measured for dDAP activity using the GFpNA activity assay. No activity was detected in the column flow-through fraction eluting from the column. This indicated near quantitative binding of the dDAP enzyme to the resin. The dDAP level applied to this column corresponded to about 1 unit per cm$^3$ (or 5 units per cm$^2$).

EXAMPLE 5

Conversion of GFpNA to pNA using Immobilized dDAP

To the column, prepared as described in Example 4, was applied a 1.0 ml solution of 0.4 mM GFpNA in 0.05M acetic acid, pH 3.5 at a flow rate of 60 cm/hr. The column effluent was monitored at 410 nm using an LKB monitor (Model 2151 Variable Wavelength Monitor set at 1.56 AUFS with a 10 mm flow cell). As the solution proceeded down the column, it became yellow in color, and as it left the column an increase in absorbance was detected. Both observations indicated that the dDAP column converted GFpNA to the chromogenic product pNA. This system of 1.0 ml injections of GFpNA on to the 1.0 ml (0.5×5.0 cm) immobilized dDAP column was used periodically to monitor the continued availability of the dDAP enzyme on the resin.

EXAMPLE 6

Conversion of Met-Arg-Human proinsulin Analog (B28 Lys, B29 Pro)

The column, prepared as described in Example 4, was re-equilibrated with about 10 column volumes of dilute acetic acid. A 20 gm/l solution of recombinantly produced MR-KPB-hPI was obtained and adjusted to pH 3.3 with 10% v/v hydrochloric acid solution. A 5.0 ml portion of the MR-KPB-hPI solution was applied to the dDAP column at room temperature at a flow rate of 60 cm/hr. The effluent was collected as 1.0 ml fractions and were diluted into 4.0 ml of 0.05M acetic acid containing 7M urea. The extent of conversion of MR-KPB-hPI to KPB-hPI was monitored on a reverse phase HPLC analytical system consisting of an Ultrasphere ODS column (Phenomenex) column eluted with a gradient of 25 to 30% acetonitrile in 0.1M ammonium phosphate, pH 7. A conversion of 40% was determined by HPLC analysis.

A second 5.0 ml portion of MR-KPB-hPI was applied to the dDAP column at a flow rate of 60 cm/hr and a percentage conversion of 40% was determined by HPLC.

A third 50 ml portion of MR-KPB-hPI was applied at a flow rate of 60 cm/hr. The portion was continuously recycled for a total of 250 ml and a final percentage conversion of 75% was determined by HPLC for the portion.

A forth 5.0 ml portion of HR-KPB-hPI was applied at a flow rate of 12 cm/hr and a percentage conversion of 83% was determined by HPLC.

A fifth 60 ml portion of MR-KPB-hPI was applied at a flow rate of 12 cm/hr and a percentage conversion of 80% was determined by HPLC.

A sixth 148 ml portion of MR-KPB-hPI was applied at an average flow rate of 12 cm/hr and an average percentage conversion of 84% was determined by HPLC.

A total of 15 days elapsed during the course of the above described experiment. When the column was not exposed to the MR-KPB-hPI solution, it was washed and stored in dilute acetic acid at room temperature (20° C.). During the application of the final 213 ml of MR-KPB-hPI, when the flow was maintained at a constant 8 cm/hr, no significant decrease in percentage conversion of MR-KPB-hPI was detected suggesting that further additional amounts of MR-KPB-hPI could be processed over this resin with continued good yield. Occasional buildups of column back pressure were encountered during the course of this experiment; however, a temporary reversal of column flow or column frit replacements appeared to correct this problem. The dDAP on the column was exposed to the equivalent of about five standard batch-mode MR-KPB-hPI conversion reactions (273 ml or about 5.5 gm of MR-KPB-hPI was reacted in this experiment). In batch mode, about 50–60 ml or about 1.0 gm, of MR-KPB-hPI would be reacted with 1 unit of dDAP. This observation supported the contention that dDAP immobilized in this manner made a significant impact on dDAP usage by the MR-KPB-hPI process.

EXAMPLE 7

Preparation of Larger Immobilized dDAP Columns

Columns measuring 1.0×6.0 cm, 2.2×6.0 cm, and 30×10 cm were individually packed with Q Sepharose® Big Bead resin (Pharmacia Chemical Company) and equilibrated with 5 column volumes of dilute acetic acid (0.05M acetic acid, pH 3.5). A solution of purified dDAP (9.5 U per ml), prepared and isolated in accordance with Examples 1 and 2, was diluted to 4 U per ml in dilute acetic acid. The dDAP solution was individually applied to each different column at a flow rate of 50 cm/hr. The dDAP was applied in levels of 2.5 U per cm$^2$ (1.0×6.0 cm), 5.0 U per cm$^2$ (1.0×6.0 cm), and 10.0 U per cm$^2$ (1.0×6.0 cm, 2.2×6.0 cm, and 30×10 cm). Each column was washed with at least 3 additional column volumes of dilute acetic acid. The column flow-through for each column was measured for dDAP activity using the GFpNA activity assay. No activity was detected in the column flow-through fraction eluting from the column. This indicated near quantitative binding of the dDAP enzyme to the resin.

EXAMPLE 8

Conversion of Met-Arg-Human Proinsulin Analog (B28 LyS, B29 PrO)

A 1.0×6.0 cm dDAP column, prepared as described in Example 7, was washed with at least 3 column volumes of dilute acetic acid. A 17 gm/l solution of partially purified recombinant MR-KPB-hPI was adjusted to pH 3.5 with 10% v/v hydrochloric acid solution or 10% w/v sodium hydroxide solution. 2000 ml of the MR-KPB-hPI solution was applied at room temperature (20°–22° C.) at various linear flow rates (8 to 115 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont Zorbax®, octyldimethylsilane-derivatized porous silica microsphere particles, 5 micron 300 Å column (15×4.6 cm). The column was eluted with a morpholine/phosphate/OSA buffer system using an ACN gradient.

The relationship between the flow rate and yield was determined based on the averages of 6 different linear flow rates. The column performance was monitored by periodic evaluation of the yield at 76 cm/hr and was found to be between 54 and 61%.

After a 19 day storage period, a second run was made on the column by passing a 400 ml portion of MR-KPB-hPI across the column. The yield at 76 cm/hr was 55%.

45 days from the first conversion, a third run was made by passing a 600 ml portion of MR-KPB-hPI across the column. The yield at 76 cm/hr, based on 2 effluent samples, was 46–52%.

When not in use, the column was washed and stored in dilute acetic acid, pH 3.5 at room temperature (about 20° C.). During the application of MR-KPB-hPI described above, minimal decrease in percentage conversion of MR-KPB-hPI was measured.

During the conversion runs described above in Example 8, the immobilized dDAP on the column was exposed to the equivalent of 7.5 standard batch-mode MR-KPB-hPI conversion reactions. This translated to a total of 3000 ml (approximately 51 gm) of MR-KPB-hPI that was converted in these experiments. In contrast, 8 units of dDAP used as the free enzyme in a batch mode process would only convert 400 ml (approximately 6.8 gm) of MR-KPB-hPI in a given time window. This calculation demonstrated that the presently claimed method is more efficient than a batch mode process.

EXAMPLE 9

Conversion of Met-Arg-Human Proinsulin Analog (B28 LVs, B29 Pro) at Varying Concentrations A 1.0×6.0 cm dDAP column, prepared as described in Example 7, was washed with at least 3 column volumes of dilute acetic acid. A 17 gm/l solution of partially purified recombinant MR-KPB-hPI was adjusted to pH 3.5 with 10% v/v hydrochloric acid solution or 10% w/v sodium hydroxide solution. A 17 gm/l solution of MR-KPB-hPI was diluted to about 3.4 mg/ml and 0.85 mg/ml with dilute acetic acid.

The 17 mg/ml, 3.4 mg/ml, and 0.85 mg/ml solutions of MR-KPB-hPI were applied at room temperature (20°–22° C.) at various linear flow rates (115, 76, and 23 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont Zorbax® 5 micron 300 Å column (15×4.6 cm). The column was eluted with a morpholine/phosphate/OSA buffer system using an ACN gradient.

The relationship between the yield and flow rate was essentially identical for each substrate concentration. (At a flow rate of 115 cm/hr, the yields for the 17, 3.4, and 0.85 gram per liter solutions were 48%, 50%, and 50% respectively. At a flow rate of 76 cm/hr, the yields for the 17, 3.4, and 0.85 mg/ml solutions were 55%, 58%, and 58% respectively. At a flow rate of 23 cm/hr, the yields for the 17, 3.4, and 0.85 mg/ml solutions were 83%, 89%, and 85% respectively.) This demonstrated that the conversion yield was not a function of substrate concentration when using a 10 U per cm$^2$ immobilized dDAP column.

EXAMPLE 10

Conversion of Met-Arg-Human Proinsulin Analog (B28 Lys, B29 Pro) Using a Reslurried dDAP Column The resin in the column used in Example 8 was reslurried with 1 column volume of dilute acetic acid. The column was packed and washed with at least 3 column volumes of dilute acetic acid. A 17 gm/l solution of partially purified MR-KPB-hPI was adjusted to pH 3.5 with 10% v/v hydrochloric acid solution or 10% w/v sodium hydroxide solution.

The MR-KPB-hPI solution was applied at room temperature (20°–22° C.) at various linear flow rates (115, 76, 8, 23, 10, and 4 cm/hr). Effluent samples were collected for each flow rate after at least 2 column volumes had passed through the column. The extent of conversion of MR-KPB-hPI to KPB-hPI was monitored on a reverse phase HPLC analytical system consisting of a Dupont Zorbax® 5 micron 300 Å column (15×4.6 cm). The column was eluted with a morpholine/phosphate/OSA buffer system using an ACN gradient.

The relationship between the yield and flow rate was essentially identical to the yields before the reslurry. At a flow rate of 115 cm/hr, the yield was 39%, as compared to 38–41% on the column before reslurry.

EXAMPLE 11

Scaled-up Conversion of Met-Arg-Human Proinsulin Analog (B28 Lys, B29 Pro)

The 7 L (30×10 cm) immobilized dDAP column prepared as described in Example 7 at 10 U per cm$^2$ was washed with at least 4 column volumes of dilute acetic acid, pH 3.5. 218 liters of a 16 gm/l solution of partially purified MR-KPB-hPI (approximately 3488 gm) was adjusted to pH 3.5 with 10% v/v hydrochloric acid solution or 10% w/v sodium hydroxide solution. The MR-KPB-hPI solution was warmed from 4° C. to 21° C., and the temperature was maintained at 21° C. during the processing time (30–35 hours). The solution was applied to the column at 10 cm/hr. Samples of the effluent and charge were taken every 2 hours to monitor the conversion reaction. After the MR-KPB-hPI solution was depleted, the column was washed with 3 column volumes of dilute acetic acid, pH 3.5 at 10 cm/hr. The first column volume was collected and stored with the KPB-hPI effluent, and the column was stored in dilute acetic acid at 21° C.

The extent of conversion of MR-KPB-hPI to KPB-hPI was monitored on a reverse phase HPLC analytical system consisting of a Dupont Zorbax® 5 micron 300 Å column (15×4.6 cm) at 35° C. The column was eluted with an isocratic morpholine/OSA/ACN buffer system. The A buffer (25% ACN) and B buffer (50% ACN) mixture was maintained at 38–42% ACN. The conversion yield across the column averaged about 98%.

After 11 days, the column was flushed with at least column volumes of dilute acetic acid at 20° C. The column flow-through was measured for dDAP activity using the GFpNA activity assay. No activity was detected in the column flow-through fraction that eluted from the column, indicating no significant leaching of active dDAP from the column resin.

242 liters of a 17.5 gm/l solution of partially purified MR-KPB-hPI was obtained and adjusted to pH 3.5 with 10% v/v hydrochloric acid solution or 10% w/v sodium hydroxide solution. The temperature of the MR-KPB-hPI solution was maintained at 2°–4° C. during the processing time (30–35 hours). An in-line heat exchanger was used to warm the MR-KPB-hPI charge to 20°–22° C. The solution was applied to the column at 10 cm/hr.

Samples of the effluent and charge were taken every 2 hours to monitor the conversion reaction. After the MR-KPB-hPI was depleted, the column was flushed with 3 column volumes of dilute acetic acid at 10 cm/hr. The first column volume was collected and stored with the KPB-hPI effluent, and the other two column volumes were collected as waste. The column was stored in dilute acetic acid at 20° C.

The extent of conversion of MR-KPB-hPI to KPB-hPI was monitored on a reverse phase HPLC analytical system consisting of a Dupont Zorbax® C-8, 5 micron 300 Å column (15×4.6 cm) at 35° C. The column was eluted with an isocratic morpholine/OSA/ACN buffer system. The A buffer (25% ACN) and B buffer (50% ACN) mixture was maintained at 38–42% ACN. The conversion yield across the column averaged about 92%.

EXAMPLE 12

Covalent Immobilization of dDAP and Its Use in Processing Met-Asp-Human Growth Hormone One gram of CH Sepharose® 4B (Pharmacia) was swelled in 100 mM acetic acid, pH 5. One mL of the swelled resin was washed extensively with additional 100 mM acetic acid, pH 5. A 1:1 (v/v) slurry of resin and buffer was prepared to which 23 mU of purified dDAP (prepared in accordance with Examples 1 and 2) was added. The mixture was gently mixed by inversion for about 18 hours at 4° C. The resin was then packed, at room temperature, in a 0.5×5 cm (1.0 mL) column (Pharmacia® HR 5/5) and washed down flow at 0.2 mL/min (16.7 cm/hr) with 2.0 mL of 0.5M Tris®, pH 7. The Tris® buffer was allowed to incubate with the resin for an additional 30 minutes to allow quenching of remaining activated sites. The column was further washed down flow with 2.0 mL of 0.05M acetic acid, pH 3.5; 2 mL of 0.5M Tris®, 0.5M NaCl, pH 7; and 4.0 mL of 0.05M acetic acid, pH 3.5 to prepare and equilibrate the column for contact with precursor protein.

Met-Asp-hGH was produced as an insoluble protein in the cytoplasm of *E. coli*. The insoluble protein was solubilized, folded to produce proper disulfide-paired Met-Asp-hGH and purified by ion-exchange chromatography. This preparation was solvent exchanged and adjusted to pH 3.5 for use as the precursor protein solution for the immobilized dDAP column. The absorbance of the solution at 280 nm was used to determine that the approximate concentration of Met-Asp-hGH was 5 mg/mL.

The Met-Asp-hGH precursor protein solution (5 mg) was applied to the column at a linear flow rate of 1.25 cm/hr. The column flow-through was diluted ten-fold in a solution of 100 mM Tris®, 30% acetonitrile, pH 8 and assayed by reverse phase chromatography and a human growth hormone (hGH) conversion yield of 37% was determined. Further experiments showed that an additional 60 mg of Met-Asp-hGH solution could be processed over this column with an average hGH yield of 33%. Periodic sampling of the column flow-through indicated that the hGH yield was consistent throughout the run. A total of 65 mg of Met-Asp-hGH was processed.

In a batch-mode reaction, about 390 mU of dDAP would be required to process 65 mg of Met-Asp-hGH. The experiment demonstrated the feasibility of using covalently immobilized dDAP to process Met-Asp-hGH to hGH with a many-fold decrease in dDAP use as compared to a batch-mode conversion reaction.

EXAMPLE 13

Recycle end Discrete Pass Conversion of Met-Arg-Human Proinsulin Analog (B28 Lys, B29 Pro)

A column measuring 0.5×5 cm was prepared as described in Example 7 with a level of dDAP equivalent to 10 units per cm$^2$. A solution (approximately 17 g/L) of partially purified recombinant MR-KPB-hPI was adjusted to pH 3.5 with 10% v/v hydrochloric acid solution or 10% w/v sodium hydroxide solution. The MR-KPB-hPI solution was charged to the column at room temperature (20°–22° C.) at 100 cm/hr. After approximately 8 column volumes, the effluent was continuously recycled back to the charge container. Samples were periodically taken from the charge container.

The extent of conversion of MR-KPB-hPI to KPB-hPI was monitored on a reverse phase HPLC analytical system consisting of a Dupont Zorbax® 5 micron 300 Å column (15×4.6 cm). The column was eluted with a morpholine/phosphate/OSA buffer system using an ACN gradient. The yield after 1, 2, and 3 pass equivalents (total volume across the column divided by the total volume of solution in the charge container and lines) was 58%, 71%, and 80% respectively.

The previously prepared column was washed with at least 3 column volumes of dilute acetic acid. The previously prepared MR-KPB-hPI solution was charged to the column at room temperature (20°–22° C.) at flow rates of 150 cm/hr and 50 cm/hr. The effluent was collected and re-charged across the column for 2 to 3 additional discrete passes. Effluent samples were taken after each discrete pass. The extent of conversion of MR-KPB-hPI to KPB-hPI was monitored on the previously described analytical system. The cummulative yield after each discrete pass was 59%, 81%, and 85% at 150 cm/hr; 75%, 86%, 86%, and 89% at 50 cm/hr.

This demonstrated that a desired conversion step yield can be obtained at higher linear flow rates by recycling the column effluent or by discrete passes across a single column.

EXAMPLE 14

Conversion of Met-Arg-Human Proinsulin Analog (B28 Lys, B29 Pro) using Immobilized Columns in Series Three columns measuring 0.5×4.5 cm were prepared individualy as described in Example 7 with a level of dDAP equivalent to 10 units per cm$^2$. The columns were connected in series and washed with at least 3 column volumes of dilute acetic acid. A solution (approximately 17 g/L) of partially purified recombinant MR-KPB-hPI was adjusted to pH 3.5 with 10% v/v hydrochloric acid solution or 10% w/v sodium hydroxide solution. The MR-KPB-hPI solution was charged to the columns at room temperature (20°–22° C.) at 40–50 cm/hr.

The extent of conversion of MR-KPB-hPI to KPB-hPI was monitored on a reverse phase HPLC analytical system consisting of a Dupont Zorbax® 5 micron 300 A column (15×4.6 cm). The column was eluted with a morpholine/phosphate/OSA buffer system using an ACN gradient. The yield ranged from 84% to 90%.

This demonstrated that a desired conversion step yield can be obtained at higher linear flow rates by utilizing multiple columns in series.

We claim:

1. A method for removing an amino-terminal dipeptide from a precursor polypeptide to produce a polypeptide product, which precursor polypeptide comprises a dipeptide extended from a peptide bond, which is to be, after removal of said dipeptide, an amino terminus of said polypeptide product, said method comprising:

a) immobilizing onto a suitable support surface an approximately 225 kilodalton dipeptidylaminopeptidase (dDAP) which is isolated from *Dictyostelium discoideum* and has a pH optimum of approximately 3.5;

b) contacting said precursor polypeptide with said immobilized dDAP under conditions sufficient to allow the action of said immobilized dDAP to remove said amino-terminal dipeptide from said precursor polypeptide to produce said polypeptide product; and c) recovering the polypeptide product.

2. The method of claim 1 wherein the precursor polypeptide is selected from the group consisting of a precursor of human proinsulin, a precursor of an analog of human proinsulin, and a precursor of human growth hormone.

3. The method of claim 1 wherein the precursor polypeptide is selected from the group consisting of Met-Asp-human growth hormone, Met-Arg-human growth hormone, Met-Arg-Human Proinsulin, Met(O)-Arg-Human Proinsulin, Met-Tyr-Human Proinsulin, -Met-Arg-Human Proinsulin Analog, -Met-Tyr-Human Proinsulin Analog, -Met-Arg-Human Proinsulin Analog, -Met-Tyr-Human Proinsulin Analog, and des 64-Met-Tyr-Human Proinsulin Analog.

4. The method of claim 3 wherein the precursor polypeptide is -Met-Arg-Human Proinsulin Analog.

5. The method of claim 3 wherein the precursor polypeptide is Met-Asp-human growth hormone.

6. The method of claim 1 wherein the dDAP is non-covalently immobilized to the support surface.

7. The method of claim 6 wherein the precursor polypeptide is selected from the group consisting of a precursor of human proinsulin, a precursor of an analog of human proinsulin, and a precursor of human growth hormone.

8. The method of claim 6 wherein the precursor polypeptide is selected from the group consisting of Met-Asp-human growth hormone, Met-Arg-human growth hormone, Met-Arg-Human Proinsulin, Met(O)-Arg-Human Proinsulin, Met-Tyr-Human Proinsulin, -Met-Arg-Human Proinsulin Analog, -Met-Tyr-Human Proinsulin Analog, -Met-Arg-Human Proinsulin Analog, -Met-Tyr-Human Proinsulin Analog, and des 64-Met-Tyr-Human Proinsulin Analog.

9. The method of claim 8 wherein the precursor polypeptide is -Met-Arg-Human Proinsulin Analog.

10. The method of claim 9 wherein the support surface is trimethylaminomethyl substituted beaded agarose.

11. The method of claim 1 wherein the dDAP is covalently immobilized to the support surface.

12. The method of claim 11 wherein the precursor polypeptide is selected from the group consisting of a precursor of human proinsulin, a precursor of an analog of human proinsulin, and a precursor of human growth hormone.

13. The method of claim 11 wherein the precursor polypeptide is selected from the group consisting of Met-Asp-human growth hormone, Met-Arg-human growth hormone, Met-Arg-Human Proinsulin, Met(O)-Arg-Human Proinsulin, Met-Tyr-Human Proinsulin, -Met-Arg-Human Proinsulin Analog, -Met-Tyr-Human Proinsulin Analog, -Met-Arg-Human Proinsulin Analog, -Met-Tyr-Human Proinsulin Analog, and des 64-Met-Tyr-Human Proinsulin Analog.

14. The method of claim 13 wherein the precursor polypeptide is Met-Asp-Human Growth Hormone.

15. The method of claim 1 wherein the precursor polypeptide is repeatedly contacted with the immobilized dDAP in the form of a bed.

16. The method of claim 15 wherein the precursor polypeptide is recycled one or more times over said bed of immobilized dDAP.

17. The method of claim 15 wherein the precursor polypeptide is sequentially passed over two or more of said beds of immobilized dDAP.

18. The method of claim 17 wherein the immobilized dDAP bed is prepared using trimethylaminomethyl substituted beaded agarose and the precursor polypeptide is -Met-Arg-Human Proinsulin Analog which is sequentially passed over three separate trimethylainomethyl substituted beaded agarose dDAP beds.

19. A method for removing amino-terminal dipeptides from a precursor polypeptide to produce a polypeptide product, which precursor polypeptide comprises an even number of amino acids extended from a peptide bond, which is to be, after removal of said dipeptides, an amino terminus of said processed polypeptide, said method comprising:

a) immobilizing onto a suitable support surface an approximately 225 kilodalton dipeptidylaminopeptidase (dDAP) which is isolated from *Dictyostelium discoideum* and has a pH optimum of approximately 3.5;

b) contacting said precursor polypeptide with said immobilized dDAP under conditions sufficient to allow the action of said immobilized dDAP to sequentially remove said amino-terminal dipeptides from said precursor polypeptide to produce said polypeptide product; and c) recovering the polypeptide product.

20. The method of claim 19 wherein the precursor polypeptide is selected from the group consisting of a precursor of human proinsulin, a precursor of an analog of human proinsulin, and a precursor of human growth hormone.

* * * * *

UNITED STATES PATENT AND TRADEMARK OFFICE
CERTIFICATE OF CORRECTION

PATENT NO. : 5,573,923  Page 1 of 2
DATED : November 12, 1996
INVENTOR(S) : Paul R. Atkinson and Lisa K. Foster It is certified that error appears in the above-indentified patent and that said Letters Patent is hereby corrected as shown below:

Column 18, line 5, after "Proinsulin," insert --[Lys$^{B28}$, Pro$^{B29}$]--.

Column 18, line 6, after "Analog," insert --[Lys$^{B28}$, Pro$^{B29}$]--.

Column 18, line 6, after "Analog," (second instance) insert --[Asp$^{B10}$, des$^{B28-30}$]--.

Column 18, line 7, after "Analog," insert --[Asp$^{B10}$, des$^{B28-30}$]--.

Column 18, line 10, after "is" insert [Lys$^{B28}$, Pro$^{B29}$]--.

Column 18, line 23, after "Proinsulin," insert --[Lys$^{B28}$, Pro$^{B29}$]--.

Column 18, line 24, after "Analog," insert --[Lys$^{B28}$, Pro$^{B29}$]--.

Column 18, line 24, after "Analog," (second instance) insert --[Asp$^{B10}$, des$^{B28-30}$]--.

Column 18, line 25, after "Analog," insert --[Asp$^{B10}$, des$^{B28-30}$]--.

Column 18, line 28, after "is" insert --[Lys$^{B28}$, Pro$^{B29}$]--.

Column 18, line 42, after "Proinsulin," insert --[Lys$^{B28}$, Pro$^{B29}$]--.

Column 18, line 43, after "Analog," insert --[Lys$^{B28}$, Pro$^{B29}$]--.

Column 18, line 43, after "Analog," (second instance) insert --[Asp$^{B10}$, des$^{B28-30}$]--.

UNITED STATES PATENT AND TRADEMARK OFFICE
CERTIFICATE OF CORRECTION

PATENT NO. : 5,573,923

DATED : November 12, 1996

INVENTOR(S) : Paul R. Atkinson and Lisa K. Foster

It is certified that error appears in the above-indentified patent and that said Letters Patent is hereby corrected as shown below:

Column 18, line 44, after "Analog," insert --[Asp$^{B10}$, des$^{B28-30}$]--.

Column 18, line 60, after "is" insert --[Lys$^{B28}$, Pro$^{B29}$]--.

Signed and Sealed this

First Day of April, 1997

Attest:

BRUCE LEHMAN

Attesting Officer

Commissioner of Patents and Trademarks